(12) United States Patent
Yin et al.

(10) Patent No.: US 10,577,678 B2
(45) Date of Patent: Mar. 3, 2020

(54) FULLY ALLOYED AG—AU NANOSTRUCTURES

(71) Applicant: The Regents of the University of California, Oakland, CA (US)

(72) Inventors: Yadong Yin, Riverside, CA (US); Chuanbo Gao, Shaanxi (CN)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 520 days.

(21) Appl. No.: 15/309,349

(22) PCT Filed: May 7, 2015

(86) PCT No.: PCT/US2015/029687
§ 371 (c)(1),
(2) Date: Nov. 7, 2016

(87) PCT Pub. No.: WO2015/171892
PCT Pub. Date: Nov. 12, 2015

(65) Prior Publication Data
US 2017/0073796 A1    Mar. 16, 2017

Related U.S. Application Data

(60) Provisional application No. 61/990,018, filed on May 7, 2014.

(51) Int. Cl.
*B22F 9/24* (2006.01)
*C22C 5/02* (2006.01)
(Continued)

(52) U.S. Cl.
CPC .............. *C22C 5/02* (2013.01); *B22F 1/0044* (2013.01); *B22F 1/0048* (2013.01);
(Continued)

(58) Field of Classification Search
None
See application file for complete search history.

(56) References Cited

U.S. PATENT DOCUMENTS

| 7,820,064 B2 | 10/2010 | Jin |
| 2008/0206562 A1 | 8/2008 | Stucky et al. |

(Continued)

FOREIGN PATENT DOCUMENTS

WO    WO 2006/073439 A2    7/2006

OTHER PUBLICATIONS

Shi, H. et al., "Composition modulation of optical absorption in AgxAu1-x alloy nanocrystals in situ formed within pores of mesoporous silica", Journal of Applied Physics, vol. 87, No. 3, pp. 1572-1574, published online Jan. 18, 2000.*

(Continued)

*Primary Examiner* — George Wyszomierski
(74) *Attorney, Agent, or Firm* — Buchanan Ingersoll & Rooney PC (57) ABSTRACT

Alloyed Ag/Au nanospheres with high compositional homogeneity ensured by annealing at elevated temperatures show large extinction cross-sections, extremely narrow bandwidths and remarkable stability in harsh chemical environments. A critical temperature has been found to be around 930° C., below which the resulting alloy nanospheres, although significantly more stable than pure silver nanoparticles, can still gradually decay upon extended exposure to harsh etchant. The nanospheres annealed above the critical temperature show homogeneous distribution of Ag and Au elements, minimal crystallographic defects, absence of structural and compositional interfaces, which account for the extremely narrow bandwidths of the surface plasmon resonance, and may render many plasmonic applications (Continued)

with high performance and long lifetime, especially for those involving corrosive species.

10 Claims, 7 Drawing Sheets

(51) Int. Cl.

| | |
|---|---|
| *C22C 5/00* | (2006.01) |
| *B82Y 30/00* | (2011.01) |
| *B22F 1/00* | (2006.01) |
| *B22F 1/02* | (2006.01) |
| *C22F 1/14* | (2006.01) |
| *G01N 21/552* | (2014.01) |

(52) U.S. Cl.
CPC ............ *B22F 1/0085* (2013.01); *B22F 1/025* (2013.01); *B22F 9/24* (2013.01); *B82Y 30/00* (2013.01); *C22C 5/00* (2013.01); *C22F 1/14* (2013.01); *G01N 21/554* (2013.01)

(56) References Cited

U.S. PATENT DOCUMENTS

| | | | | |
|---|---|---|---|---|
| 2011/0250122 | A1* | 10/2011 | Joo | .......................... B01J 23/38 423/437.2 |
| 2011/0311635 | A1 | 12/2011 | Stucky et al. | |
| 2012/0114962 | A1 | 5/2012 | Maye et al. | |
| 2014/0308756 | A1* | 10/2014 | Gautier | ................. B22F 1/0018 436/501 |

OTHER PUBLICATIONS

Rodriguez-Gonzalez, B. et al., "AuAg bimetallic nanoparticles: formation, silica-coating and selective etching", Royal Society of Chemistry, vol. 125, pp. 133-144, published on web Jul. 24, 2003.*
Chen, T. et al., "Scalable Routes to Janus Au—SiO2 and Ternary Ag—Au—SiO2 Nanoparticles", Chem. Mater., vol. 22, pp. 3826-3828, published on web Jun. 8, 2010.*
Gao, C. et al., "Templated Synthesis of Metal Nanorods in Silica Nanotubes", JACS, vol. 133, pp. 19707-19709, published Nov. 15, 2011.*
Zong, S. et al., "A SERS and fluorescence dual modse cancer cell targeting probe based on silica coated Au@Ag coew-shell nanorods", Talanta, vol. 97, pp. 368-375, available online Apr. 30, 2012.*
M. Daniel et al., "Gold Nanoparticles: Assembly, Supramolecular Chemistry, Quantum-Size-Related Properties, and Applications toward Biology, Catalysis, and Nanotechnology", Chemical Reviews, 2004, pp. 293-346, vol. 104, No. 1.
R. Sperling et al., "Biological applications of gold nanoparticlest", Chemical Society Reviews, Jul. 17, 2008, pp. 1896-1908, vol. 37.
S. Linic et al., "Plasmonic-metal nanostructures for efficient conversion of solar to chemical energy", Nature Materials, Dec. 2011, pp. 911-921, vol. 10.
D. Aherne et al., "Etching-Resistant Silver Nanoprisms by Epitaxial Deposition of a Protecting Layer of Gold at the Edges", Langmuir Article, Jul. 7, 2009, pp. 10165-10173, vol. 25, No. 17.
X. Zhang et al., "Ultrastable Substrates for Surface-Enhanced Raman Spectroscopy: A'203 Overlayers Fabricated by Atomic Layer Deposition Yield Improved Anthrax Biomarker Detection", JACS Article, Jul. 19, 2006, pp. 10304-10309, vol. 128.
C. Gao et al., "Highly Stable Silver Nanoplates for Surface Plasmon Resonance Biosensing", Angewandte Chemie International Edition, 2012, pp. 5629-5633, vol. 51.
X. Lozano et al., "Effect of Alloying on the Optical Properties of Ag—Au Nanoparticles", The Journal of Physical Chemistry C, Jan. 17, 2013, pp. 3062-3068, vol. 117.
M. Rycenga et al., "Controlling the Synthesis and Assembly of Silver Nanostructures for Plasmonic Applications", Chemical Reviews, Mar. 11, 2011, pp. 3669-3712, vol. 111.

P. Mulvaney, "Surface Plasmon Spectroscopy of Nanosized Metal Particles", Langmuir, 1996, pp. 788-800, vol. 12, No. 3.
S. Link et al., "Spectral Properties and Relaxation Dynamics of Surface Plasmon Electronic Oscillations in Gold and Silver Nanodots and Nanorods", J. Phys. Chem. B, Sep. 10, 1999, pp. 8410-8426, vol. 103.
C. Xue et al., "Self-Assembled Monolayer Mediated Silica Coating of Silver Triangular Nanoprisms", Advanced Materials, Jul. 11, 2007, pp. 4071-4074, vol. 19.
M. Cortie et al., "Synthesis and Optical Properties of Hybrid and Alloy Plasmonic Nanoparticles", Chemical Reviews, Jan. 14, 2011, pp. 3713-3735, vol. 111.
M. Hostetler et al., "Stable, Monolayer-Protected Metal Alloy Clusters", J. Am. Chem. Soc., Aug. 28, 1998, pp. 9396-9397, vol. 120, No. 36.
S. Link et al., "Alloy Formation of Gold-Silver Nanoparticles and the Dependence of the Plasmon Absorption on Their Composition", J. Phys. Chem. B, Apr. 16, 1999, pp. 3529-3533, vol. 103, No. 18.
M. Mallin et al., "Solution-Phase Synthesis of Sub-10 nm Au—Ag Alloy Nanoparticles", Nano Letters, Oct. 2, 2002, pp. 1235-1237, vol. 2, No. 11.
A. Pal et al., "Preparation of Silver-Gold Alloy Nanoparticles at Higher Concentration Using Sodium Dodecyl Sulfate", Aust. J. Chem., 2008, pp. 66-71, vol. 61.
I. Russier-Antoine et al., "Surface heterogeneity in Au—Ag nanoparticles probed by hyper-Rayleigh scattering", Physical Review B, Jul. 21, 2008, pp. 035436-1-035436-8, vol. 78.
C. Wang et al., "One-Pot Synthesis of Oleylamine Coated AuAg Alloy NPs and Their Catalysis for CO Oxidation", Chemistry of Materials, Feb. 10, 2009, pp. 433-435, vol. 21, No. 3.
L. Shang et al., "A Facile and Controllable Strategy to Synthesize Au—Ag Alloy Nanoparticles within Polyelectrolyte Multilayer Nanoreactors upon Thermal Reduction", Langmuir Article, Dec. 17, 2009, pp. 6713-6719, vol. 26, No. 9.
B. Rodriguez-Gonzalez et al., "AuAg bimetallic nanoparticles: formation, silica-coating and selective etching", Faraday Discuss., 2004, pp. 133-144, vol. 125.
M. Shore et al., "Synthesis of Au(Core) / Ag(Shell) Nanoparticles and their Conversion to AuAg Alloy Nanoparticles", Nano Micro Small, Dec. 13, 2010, pp. 230-234, vol. 7, No. 2.
C. Wang et al., "Synthesis of AuAg Alloy Nanoparticles from Core/Shell-Structured Ag/ Au", Nano Micro Small, Feb. 2, 2009, pp. 567-570, vol. 5, No. 5.
J. Hodak et al., "Laser-Induced Inter-Diffusion in AuAg Core-Shell Nanoparticles", J. Phys. Chem., Nov. 11, 2000, pp. 11708-11718, vol. 104.
Z. Peng et al., "Laser-Assisted Synthesis of Au—Ag Alloy Nanoparticles in Solution", J. Phys. Chem. B, Jan. 25, 2006, pp. 2549-2554, vol. 110, No. 6.
X. Wang et al., "Electronic Dephasing in Bimetallic Gold-Silver Nanoparticles Examined by Single Particle Spectroscopy", J. Phys. Chem. B, Oct. 11, 2005, pp. 20324-20330, vol. 109, No. 43.
D. Radziuk et al., "Ultrasonic Alloying of Preformed Gold and Silver Nanoparticles", Nano Micro Small, Jan. 27, 2010, pp. 545-553, vol. 6, No. 4.
S. Skrabalak et al., "Gold Nanocages: Synthesis, Properties, and Applications", Accounts of Chemical Research, Dec. 2008, pp. 1587-1595, vol. 41, No. 12.
Q. Zhang et al., "Size and composition tunable Ag—Au alloy nanoparticles by replacement reactions", Nanotechnology, Dec. 2008, pp. 1-8, vol. 18.
Q. Zhang et al., "Synthesis of Monodisperse Ag—Au Alloy Nanoparticles with Independently Tunable Morphology, Composition, Size, and Surface Chemistry and Their 3-D Superlattices", Advanced Functional Materials, Apr. 1, 2009, pp. 1387-1398, vol. 19.
Y. Tang et al., "Tailoring properties and functionalities of metal nanoparticles through crystallinity engineering", Letters, Nature Materials, Aug. 19, 2007, vol. 6. (18 pages).
J. Wilcoxon, "Optical Absorption Properties of Dispersed Gold and Silver Alloy Nanoparticles", J. Phys. Chem. B, Dec. 19, 2008, pp. 2647-2656, vol. 113, No. 9.

(56) References Cited

OTHER PUBLICATIONS

T. Shibata et al., "Size-Dependent Spontaneous Alloying of Au—Ag Nano particles", JACS Articles, Sep. 13, 2002, pp. 11989-11996, vol. 124, No. 40.
C. Gao et al., "One-step seeded growth of Au nanoparticles with widely tunable sizes", Nanoscale, Mar. 11, 2012, pp. 2875-2878, vol. 4.
N. Jana et al., "Seeding Growth for Size Control of 5-40 nm Diameter Gold N anoparticles", Langmuir, Oct. 2, 2001, pp. 6782-6786, vol. 17, No. 22.
C. Gao et al., "Seeded growth route to noble metal nanostructures", Journal of Materials Chemistry C, Apr. 22, 2013. (12 pages).
C. Gao et al., "Templated Synthesis of Metal Nanorods in Silica Nanotubes", Journal of the American Chemical Society, Nov. 15, 2011, pp. 19706-19709, vol. 133.
X. Liu et al., "Size-Tailored Synthesis of Silver Quasi-Nanospheres by Kinetically Controlled Seeded Growth", Langmuir, Jul. 25, 2013, pp. 10559-10565, vol. 29.
X. Liu et al., "One-step growth of triangular silver nanoplates with predictable sizes on a large scalet", Nanoscale, Royal Society of Chemistry, Feb. 25, 2014, pp. 4513-4516, vol. 6.
M. Liu et al., "Synthesis and Optical Characterization of Au/Ag Core/Shell Nanorods", J. Phys. Chem. B, Apr. 6, 2004, pp. 5882-5888, vol. 108, No. 19.
R. Jiang et al., "Unraveling the Evolution and Nature of the Plasmons in (Au Core)-(Ag Shell) Nanorods", Advanced Optical Materials, Jun. 20, 2012, vol. 24. (8 pages).
International Search Report (PCT/ISA/210) dated Aug. 12, 2015, by the USA Patent Office as the International Searching Authority for International Application No. PCT/US2015/029687.
Written Opinion (PCT/ISA/237) dated Aug. 12, 2015, by the USA Patent Office as the International Searching Authority for International Application No. PCT/US2015/029687.

* cited by examiner

FULLY ALLOYED AG—AU NANOSTRUCTURES

CROSS-REFERENCE TO RELATED APPLICATIONS

This application claims the benefit of U.S. Provisional Application No. 61/990,018, filed May 7, 2014, the entire contents of which is hereby incorporated herein by reference,

TECHNICAL FIELD

The disclosure relates to fully alloyed Ag/Au nanospheres, which can be produced through a surface-protected annealing process.

BACKGROUND INFORMATION

Surface plasmon resonance (SPR) of metal nanoparticles has opened up emerging opportunities in a broad range of applications, such as chemical or biomolecular sensing, imaging, photothermal therapy of tumors, and sensitization in solar energy harvesting. These applications can rely on large extinction cross-sections of the nanoparticles for improved performance and high chemical stability for extended lifetime, which are highly desired and have been the goal of a long-term exploration.

It has been recognized that the plasmonic property of metal nanoparticles can be largely dependent on their intrinsic dielectric constants apart from their size, anisotropy and property of the media, so that a silver (Ag)-rich composition is essential among various metals for supporting strong surface plasmon polarization modes across the visible range of the electromagnetic spectrum, due to its highest plasmonic activity in terms of quality factor arising from its appropriate electronic structure and thus dielectric function.

Unfortunately, the excellent plasmonic property of Ag nanostructures has not been fully utilized in practical applications due to their poor chemical and structural stability against non-ideal chemical environments. To this end, methods have been developed in earlier studies such that a Ag nanostructure is stabilized for potential plasmonic applications, typically through coverage of an inorganic layer or a self-assembled organic monolayer (SAM) over a Ag nanoparticle, giving rise to a core/shell nanostructure. However, the overlayer is often vulnerable to external etchants, and prolonged exposure to them can still easily cause a loss of the stability of the Ag nanoparticles. In addition, the layer covering Ag nanostructures may often diminish the plasmonic activity of the original Ag nanostructures. Therefore, it becomes crucial to devise alternative strategies for achieving a Ag-rich nanostructure with high stability and excellent plasmonic property, for example, by alloying Ag with a chemically inert plasmonic metal such as gold (Au).

Conventionally, Ag/Au alloy nanoparticles can be synthesized by co-reduction of a mixture precursor of Ag and Au, for example, $HAuCl_4$ and $AgNO_3$. Since the formation of Ag/Au alloy nanoparticles depends on the reduction rate of the respective precursors, it is difficult to achieve compositional homogeneity of Ag and Au across an alloy nanoparticle, as indicated by more close investigations, which reveal a stepwise reduction and growth of the metals. The homogeneity can be enhanced through interdiffusion of Ag and Au into one another by means of annealing at elevated temperatures, laser radiation or ultrasonic treatment. The energy input into the nanoparticles, however, is still limited in these cases, for example, the temperature of annealing is limited to the decomposition temperature of their capping agents (oleylamine, etc.) to ensure the stability of the nanoparticle colloid, which impedes Ag and Au from efficient interdiffusion and complete alloying.

Alloy nanostructures of Ag and Au may also arise from galvanic replacement of a Ag nanoparticle with a salt of Au, which, however, can often lead to formation of nanocages or nanoframes, as well as a lack of control over the ratio and the distribution of the Ag and Au components.

Compositional inhomogeneity is expected to be present in the Ag/Au alloy nanoparticles produced by the state-of-the-art synthesis strategies, with Ag/Au ratio varying from one domain to another. On one hand, as the stability of the alloy nanoparticles heavily relies on the Ag/Au ratio, corrosion easily starts from unstable domains upon exposure to an etchant, and the stability in both morphology and optical property of the alloy nanoparticles can be significantly reduced as a result. On the other hand, the compositional domains create interfaces, which may also affect the plasmonic property of the nanoparticles.

According to Mie theory, crystalline grain boundaries in a noble metal nanoparticle can play a critical role in damping of surface plasmons and significantly enhance scattering events. In a similar manner, damping of surface plasmons can be also resulted from interfaces between domains of different compositions and thus different dielectric properties in the Ag/Au alloy nanoparticles, producing broad bandwidths of the extinction spectrum as observed in most literature reports, which add additional limitations to many of their plasmon-based applications

SUMMARY

A method for producing fully alloyed Ag/Au nanospheres is disclosed, the method comprising: forming a stock solution of Au nanoparticles; synthesizing the stock solution of Au nanoparticles into a solution comprising $AgNO_3$; obtaining a colloid of Au@Ag@$SiO_2$ nanoparticles; and annealing the colloid of Au@Ag@$SiO_2$ nanoparticles, for example, at a temperature of at least 930° C.

A method of producing fully alloyed Ag/Au nanospheres through a surface-protected annealing process is disclosed, the method comprising: performing an interfacial atomic diffusion of Ag and Au in a Au@Ag core/shell nanoparticle.

A fully alloyed Ag/Au nanospheres produced by a method as disclosed herein.

A sensor is disclosed, which includes at least a plurality of fully alloyed Ag/Au nanospheres. The plurality of fully alloyed Ag/Au nanospheres can be on a substrate, and includes circuitry for detecting molecules of interest on the substrate.

BRIEF DESCRIPTION OF THE DRAWINGS

The disclosure is explained below with reference to the exemplary embodiment shown in the drawing. In the drawing:

FIG. 4 shows a spectroscopic study of the core/shell and alloy nanoparticles, wherein (a) optical evolution of the Au@Ag core/shell nanoparticles during seeded growth of Ag on Au nanoparticles, and wherein the spectra are normalized relative to the maximum of the Au@Ag (Ag/Au=5) spectra; (b) optical evolution from Au@Ag (Ag/Au=5) core/shell nanoparticles to Ag/Au alloy nanospheres, and wherein the spectra are normalized relative to the spectral maximum of the Au@Ag core/shell nanoparticles, (c) UV-vis extinction spectra of the Ag/Au alloy nanospheres with different Ag/Au ratios, which are normalized relative to their respective maximum, and (d) Dependence of band position and full-width at half-maximum (FWHM) of extinction peaks of the Au@Ag core/shell and Ag/Au alloy nanoparticles on the Ag mole fraction.

DETAILED DESCRIPTION

In accordance with an exemplary embodiment, a plasmonic property is disclosed, which is comparable to that of pure Ag nanoparticles and significantly enhanced chemical stability, which can be achieved in fully alloyed Ag/Au nanospheres. The synthesis can be based on interfacial atomic diffusion of Ag and Au in a Au@Ag core/shell nanoparticle. To ensure complete alloying of Ag and Au, diffusion efficiency of the Ag and Au atoms can be significantly accelerated by annealing the core/shell nanoparticles at a temperature of approximately 1000° C., which is close to their respective melting points (bulk Au: 1064.2° C.; Ag: 961.8° C.) and is unprecedentedly high in the synthesis of Ag/Au alloy nanoparticles. It can be expected that atomically homogeneous distribution of Ag and Au can be conveniently established at this temperature. As no conventional surfactants can survive at such a high temperature, a layer of silica is coated on the core/shell nanoparticles prior to their annealing, serving as a high-temperature-resistant "surfactant" to prevent interparticle agglomerations, which can enable retention of the size features of the nanoparticles and eventual obtainment of monodisperse fully-alloyed Ag/Au nanoparticles as a well-dispersed colloid for potential plasmon-based applications.

Experimental Section

Synthesis of Au Nanoparticles (~15 nm)

A seeded growth route was chosen for large-scale synthesis of Au nanoparticles of a pre-determined size. A growth solution was prepared by incorporating 12 mL of PVP (5 wt %, Mw 10000), 6 mL of ascorbic acid (0.1 M), 4.5 mL of potassium iodide (0.2 M) and 1.8 mL of HAuCl4 (0.254 M) in 60 mL of $H_2O$. To this solution was quickly injected under stirring 48 mL of a seed solution (3.5-nm Au nanoparticles), which was prepared by mixing an aqueous solution containing $2.5 \times 10^{-4}$ M $HAuCl_4$ and $2.5 \times 10^{-4}$ M trisodium citrate and adding 0.6 mL of ice-cold, freshly prepared 0.1M $NaBH_4$ solution while stirring, following a literature report, and as outlined in Jana, N. R.; Gearheart, L.; Murphy, C. J. Langmuir 2001, 17, 6782-6786. After 10 minutes, the Au nanoparticles formed were collected by centrifugation and redispersed in 120 mL of $H_2O$ as a stock solution.

Synthesis of Au@Ag Core/Shell Nanoparticles

A synthesis of Au@Ag core/shell nanoparticles (Ag/Au=5), 4 mL of the Au nanoparticle (approximately 15 nm) stock solution were mixed with 15.5 mL of $H_2O$, 4.5 mL of PVP (5 wt %, Mw 10000), 15 mL of acetonitrile and 0.91 mL of ascorbic acid (0.1 M), which was followed by injection of 0.76 mL of $AgNO_3$ solution (0.1 M) at a rate of 0.05 mL/min. After 10 minutes, the Au@Ag nanoparticles were collected in 12 mL of $H_2O$.

Silica Coating

To the 12 mL of the Au@Ag core/shell nanoparticle solution was slowly added 4 mL of an ethanolic solution of 16-mercaptohexadecanoic acid (MHA, 1 mM), and the resultant solution was then mixed with 76 mL of ethanol. After that, 4 mL of diethylamine and 160 μL of TEOS were added in sequence under stirring, and the reaction was allowed to proceed for 90 min, obtaining a colloid of Au@Ag@SiO₂ nanoparticles after centrifugation and redispersion.

Annealing and Silica Removal

In a standard process, the Au@Ag@SiO₂ nanoparticles were dried and annealed at 1000° C. for 6 hours (h) in a tube furnace in $N_2$ atmosphere for effective alloying of the Ag and Au. The sample after annealing was redispersed by sonication in 40 mL of a water solution containing 1.25 wt % PVP (Mw 10000), 50 mM diethylamine and 5 mM NaOH, which was then refluxed at 100° C. for 1 h in $N_2$ atmosphere, ensuring complete removal of the silica shell. Pure Ag/Au alloy nanospheres were then collected by centrifugation and redispersed in 8 mL of $H_2O$ for future use.

Detection of Benzidine from an Artificial Industrial Waste Water by SERS

In a typical process, 20 μL of a nanoparticle solution was dried on a glass substrate in vacuum, which was then soaked in an artificial industrial waste water (MeOH 2.4 vol %, benzidine 0.5 μM, NaCl 2 wt %, $H_2O_2$ 1 mM, pH 10) for different lengths of time (10-60 min). The glass substrate was then washed, dried in vacuum, and subjected to SERS with spectra recorded for evaluation of the enhancement rendered by different noble metal nanoparticles of the same size and concentration. As all the nanoparticles investigated in this study have strong coupling at the wavelength of 633 nm (FIG. S8) after being deposited on glass substrates, the Raman signals were excited with a laser of the wavelength as much, and the scattering spectra were recorded in the range of 500-2000 $cm^{-1}$, with 10 seconds (s) of the acquisition time used for one spectrum.

Results and Discussion

In a typical synthesis, a one-step coordination-based method can be employed to afford monodisperse Au nanoparticles of a designated size in a large quantity as a starting material. Uniform coating of Ag on the Au nanoparticles can be achieved through seeded growth, with self-nucleation of Ag being suppressed in the presence of acetonitrile. The exclusive Au@Ag core/shell nanoparticles obtained were transferred to ethanol with the aid of 16-mercaptohexadecanoic acid (MHA), and then coated with a silica layer by a sol-gel reaction of tetraethyl orthosilicate (TEOS) with a tertiary amine as a catalyst to avoid possible etching of Ag. The materials were then collected, annealed at 1000° C. in nitrogen atmosphere, and treated with a solution of sodium hydroxide (NaOH) to remove silica before being transferred to water to form a stable colloid of the Ag/Au alloy nanospheres as a final product.

Figure 1:
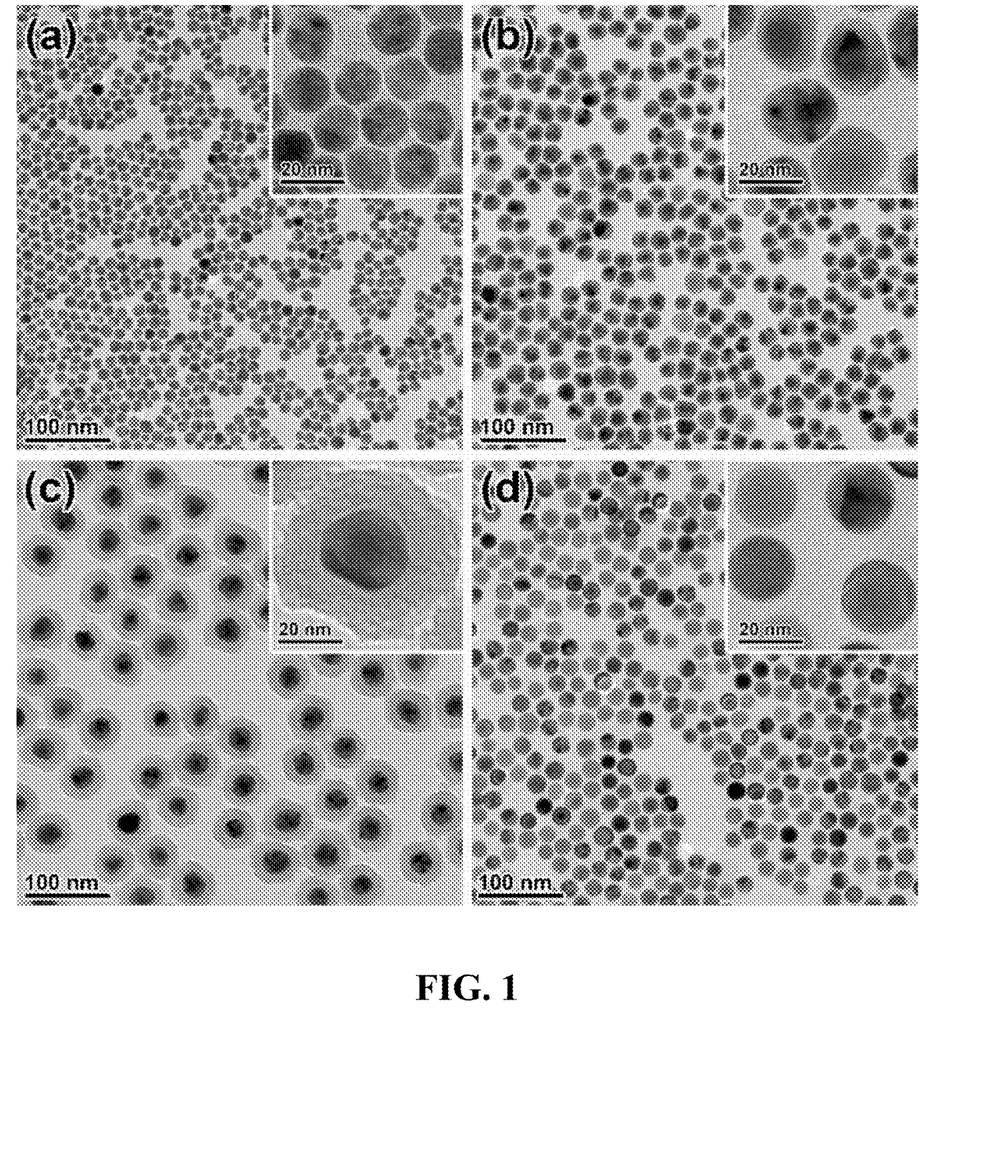
FIG. 1 shows TEM images of the Au nanoparticles (a), Au@Ag core/shell nanoparticles (b), Au@Ag@$SiO_2$ nanoparticles (c) and Ag/Au alloy nanospheres and (d), obtained from a typical synthesis of Ag/Au alloy nanospheres (Ag/Au=5).
Figure 2:
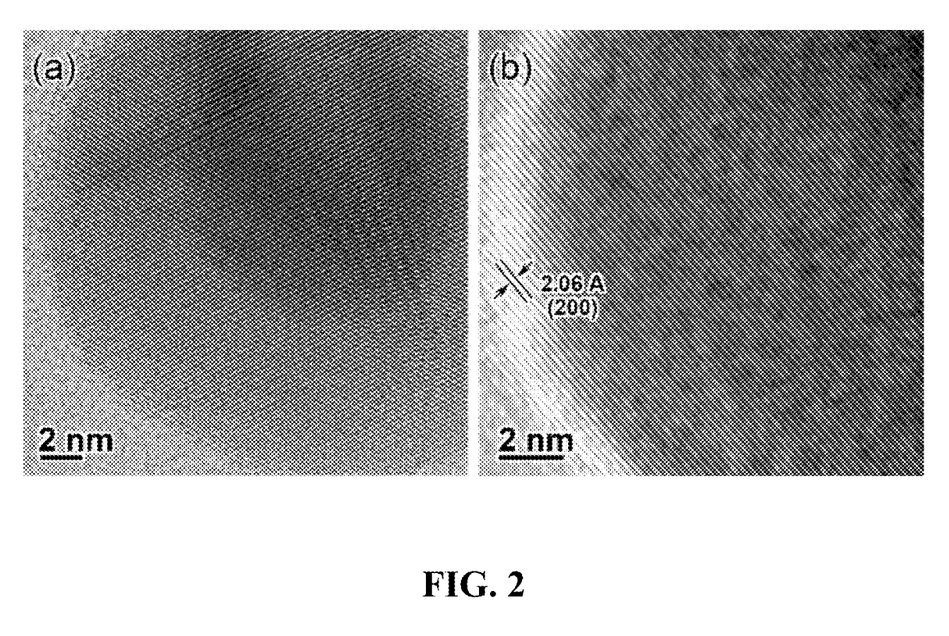
FIG. 2 shows (a) a bright-field STEM image of the Au@Ag core/shell nanosphere (Ag/Au=5), demonstrating epitaxial growth of Ag on the Au core, and (b) an HRTEM image of the Ag/Au alloy nanosphere (Ag/Au=5), showing the single crystallinity of the particle.
Figure 3:
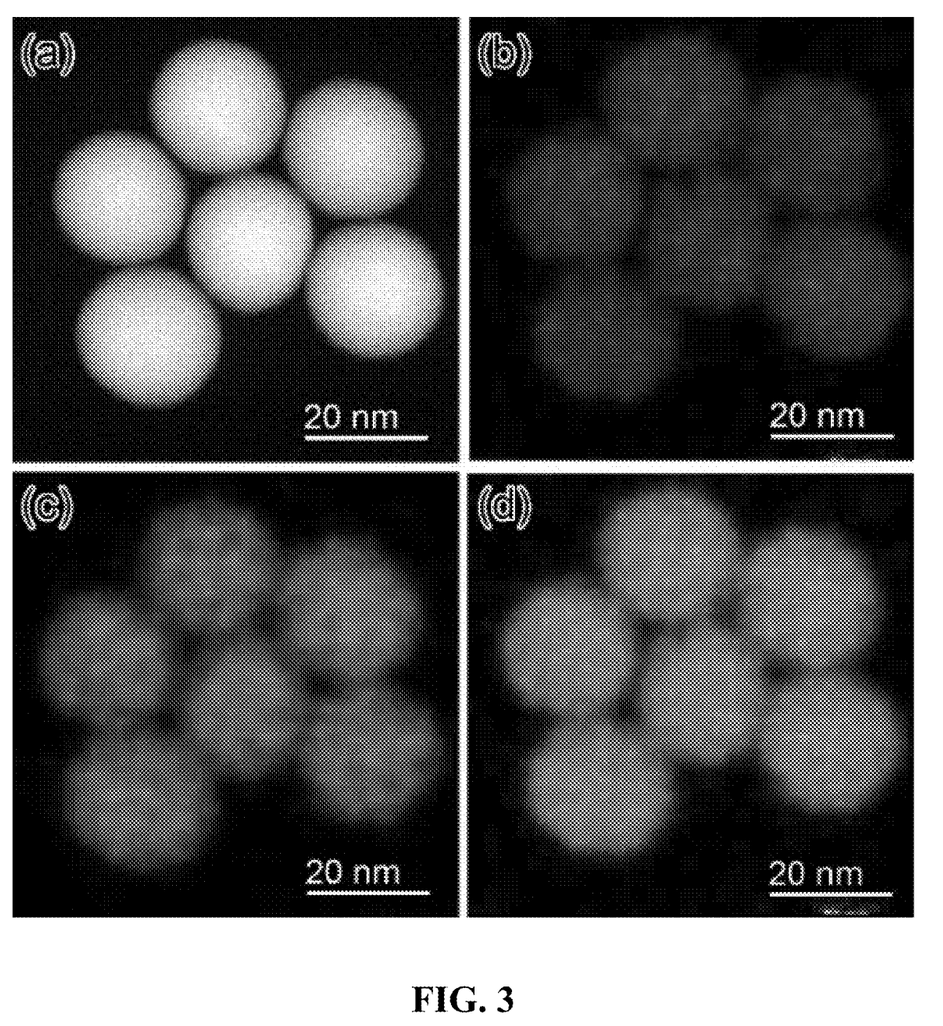
FIG. 3 shows an elemental analysis of the Ag/Au alloy nanospheres (Ag/Au=5), wherein (a) a dark-field STEM image, (b-c) Elemental mapping of Au and Ag, respectively, and (d) Merged image of (b) and (c).

FIG. 1 shows transmission electron microscopy (TEM) characterization of the Ag/Au alloy nanospheres and their synthesis intermediates (nominal ratio of Ag/Au=5). After seeded growth of Ag over Au nanoparticles of 15 nm (FIG. 1a), Au@Ag core/shell nanostructures have been formed in high yield, which is indicated by a clear Z-contrast boundary in TEM (FIG. 1b) and unambiguously confirmed by dark-field scanning electron microscopy (DF-STEM) and energy-dispersive X-ray spectroscopy (EDX) elemental mapping. An increase in particle size to 22 nm was also observed and lattice matching between the Au core and the Ag shell due to an epitaxial growth mechanism (FIG. 2a). After silica coating, an amorphous silica layer of approximately 15 nm thick forms on the surface of the metal nanoparticles without discernible etching to Ag due to the use of a tertiary amine instead of commonly used ammonia as a catalyst (FIG. 1c). After high-temperature annealing at 1000° C. and silica etching, a colloid of uniform Ag/Au alloy nanoparticles of 22 nm are obtained (FIG. 1d). The absence of large particles confirms the effective protection of the silica layer at the elevated temperature. The high-temperature annealing can be found to affect a number of features of the metal nanoparticles, including their morphology, structure and composition. For example, first, the metal nanoparticles after annealing are near perfect nanospheres (FIG. 1d) in contrast to the irregular shapes of the original core/shell ones (FIG. 1c), which can be attributed to the reshaping of the metal nanospheres due to an enhanced mobility of the metal atoms at high temperatures, and the high glass transition temperature of silica such that it remains robust at a high temperature for maintaining continuous coating of the metal nanospheres and allowing the reshaping of the metal particles. Second, high-resolution TEM (HRTEM) images (FIG. 2b) show that the alloy nanospheres after annealing are single crystals although a few planar defects can be occasionally observed, which is distinct from the original core/shell ones as they are basically polycrystalline (FIG. 1a-c). It can be ascribed to a release of crystallographic defects as a result of high atomic mobility of the metals at a high temperature, which represents an effective pathway for achieving single crystalline metal nanoparticles. Most importantly, the high-temperature annealing can greatly accelerate the diffusion rates of Ag and Au atoms and make complete mixing of the two metals possible on atomic scales, which leads to fully alloyed nanospheres, as evidenced by the complete overlap of the elemental distribution of Ag and Au in EDX mapping (FIG. 3).

Figure 4:
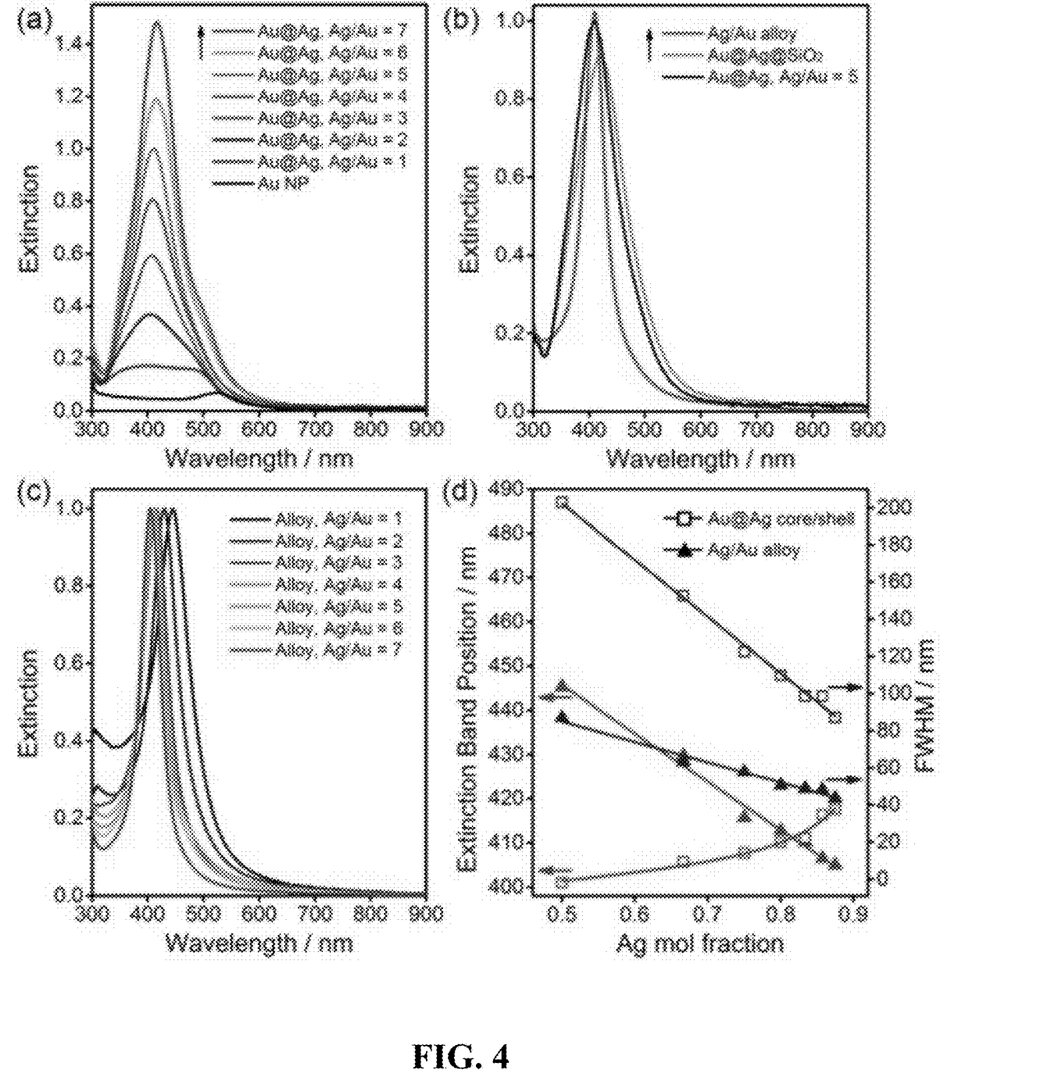

In accordance with an exemplary embodiment, the spectral properties of the Ag/Au alloy nanospheres and their synthesis intermediates were further investigated (FIG. 4). For example, when a thin layer of Ag was coated on the Au nanoparticles, a peak arises which can be analogous to a combination of the spectra from respective Au and Ag, making the overall spectrum a relatively broad one (FIG. 4a). The broadening can be attributed to the scattering effect of the Ag/Au boundary on the conduction electrons, which can lead to damping of the surface plasmons. The abrupt change of the spectral feature can suggest that the optical response of a noble metal nanoparticle is very sensitive to its outer-shell composition. Further coating of a thick Ag layer can produces an Ag-like resonance at a wavelength of approximately 410 nm. After silica coating, annealing and silica removal, the resultant Ag/Au alloy nanospheres show a resonance peak, which is near symmetric and is much narrower than the core/shell nanoparticles (FIG. 4b). Apparently, the monodispersity and the uniform spherical shape of the Ag/Au alloy nanospheres can contribute to their distinguished spectral features including their narrow bandwidths. More importantly, the alloy nanospheres are different from the core/shell ones in that they are single crystals containing no crystallographic defects, and the Ag and Au elements are homogeneously distributed without compositional interfaces over the whole nanoparticle. The effect of the former on the bandwidth of the resonance peaks has been demonstrated in literature, and confirmed by experimentation by investigating the spectral change of Ag nanospheres after removing crystallographic defects by high-temperature annealing relative to their as-synthesized ones. However, the effect of the latter on the bandwidth has not been reported to date in literature-related alloy nanoparticles. Conventionally synthesized Ag/Au alloy nanoparticles usually show a non-symmetric resonance peak as a result of strong coupling of the collective oscillation of conduction electrons to the interband transitions, which is a typical character of Au nanoparticles, indicating the presence of Au-rich domains in the alloy nanoparticles and thus the poor compositional homogeneity of the Ag and Au elements. It also explains that these alloy nanoparticles usually show broad extinction peaks as a result of the conduction electron scattering at the compositional interfaces, in a way similar to the scattering events at an Ag/Au boundary in an Au@Ag core/shell nanoparticle, which produces a broad resonance peak as well. Therefore, the narrow and symmetric resonance peak of the Ag/Au alloy nanospheres synthesized by high-temperature annealing approach can be attributed not only to the removal of crystallographic defects but more importantly to the elimination of compositional interfaces, suggesting that fully alloyed nanoparticles have been prepared as such with electron structure homogeneously modified during alloying. Additionally, the extinction efficiency of the alloy nanoparticles is very close to that of the Ag-like Au@Ag core/shell nanoparticles (FIG. 4b), indicating that the plasmonic property of the alloy nanoparticles is dominated by Ag, which together with the narrow bandwidth enables high performance in many plasmon-based applications.

The ratio of the Ag/Au in the alloy nanospheres can be tuned by controlling the amounts of respective precursors in the synthesis (FIG. 4c), with their plasmonic properties plotted in FIG. 4d. UV-vis spectroscopy shows that the extinction bands shift to blue upon an increase in the molar fraction of Ag, consistent with earlier reports. The bandwidth of the alloy nanospheres is also found in linear relationship with the molar fraction of Ag in the alloy nanospheres, which is much narrower than their core/shell counterparts in all cases. These data suggest that the plasmonic properties of the alloy nanospheres can be delicately manipulated by simply controlling their chemical compositions.

Figure 5:
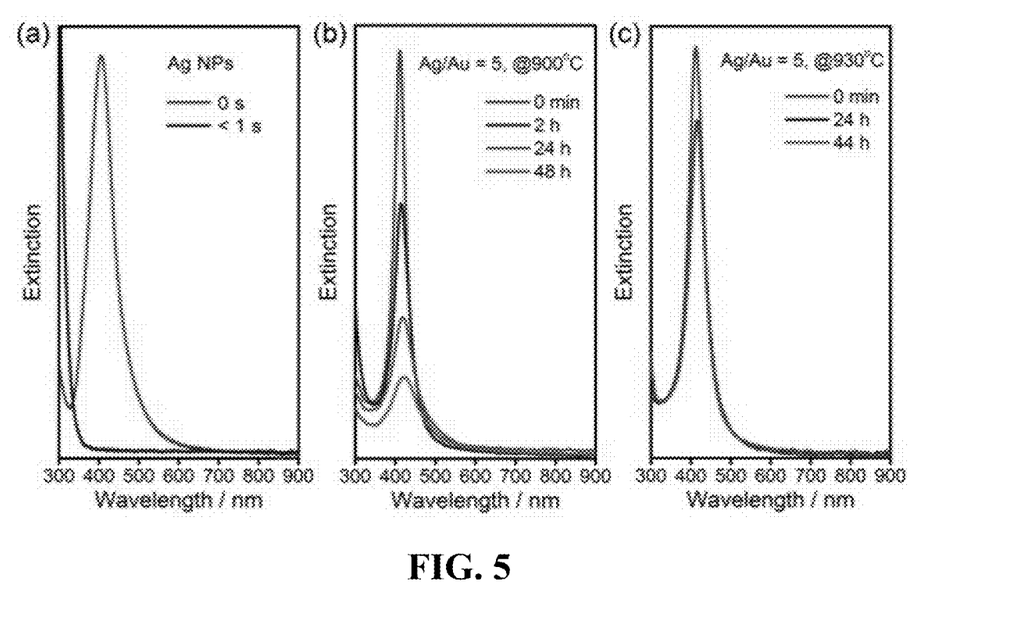
FIG. 5 shows a UV-Vis spectra showing chemical stability of (a) pure Ag nanoparticles (approximately 22 nm), (b) Ag/Au alloy nanospheres annealed at 900° C., and (c) Ag/Au alloy nanospheres annealed at 930° C., and wherein the alloy nanospheres have a Ag/Au ratio of 5, and the aqueous etchant solution is composed of $H_2O_2$ (0.5 M), $NH_3 \cdot H_2O$ (0.4 M) and PVP (surfactant, 0.5 wt %, Mw 10000), and the initial spectra (labeled as 0 s or 0 min in the figure) of the nanoparticles were recorded in the absence of $H_2O_2$ and $NH_3 \cdot H_2O$, with their volumes compensated by water

The fully alloying of Ag and Au not only improves the plasmonic property of the nanospheres but also significantly enhances the chemical stability against corrosive environments, as demonstrated by testing their stability in a mixture solution of hydrogen peroxide ($H_2O_2$) and ammonia ($NH_3$) (FIG. 5). The mixture solution contains both oxidant and complexing agents and is known as an excellent etchant for rapidly dissolving metallic Ag (within a second, FIG. 5a) but not. Au. On the other hand, the Ag/Au nanospheres, if alloyed at sufficiently high temperatures, are able to survive in this solution, with only a minor loss in plasmon band intensity even after exposure to the solution for more than 24 hours. A critical temperature was found to be around 930° C., below which the resulting alloy nanospheres, although significantly more stable than pure silver nanoparticles, still gradually decay upon extended exposure to the etchant, as shown in the case of Ag/Au alloy particles (Ag/Au=5) annealed at 900° C. (FIG. 5b). When annealed at 930° C., the alloy nanospheres can maintain their plasmon band intensity at approximately 82% of the original value after 24 hours of etching, and there was no further decay within an additional 20 hours. In order to ensure reproducibility by minimize the effect of temperature fluctuation during annealing, 1000° C. was used as the standard annealing temperature in this work.

Figure 6:
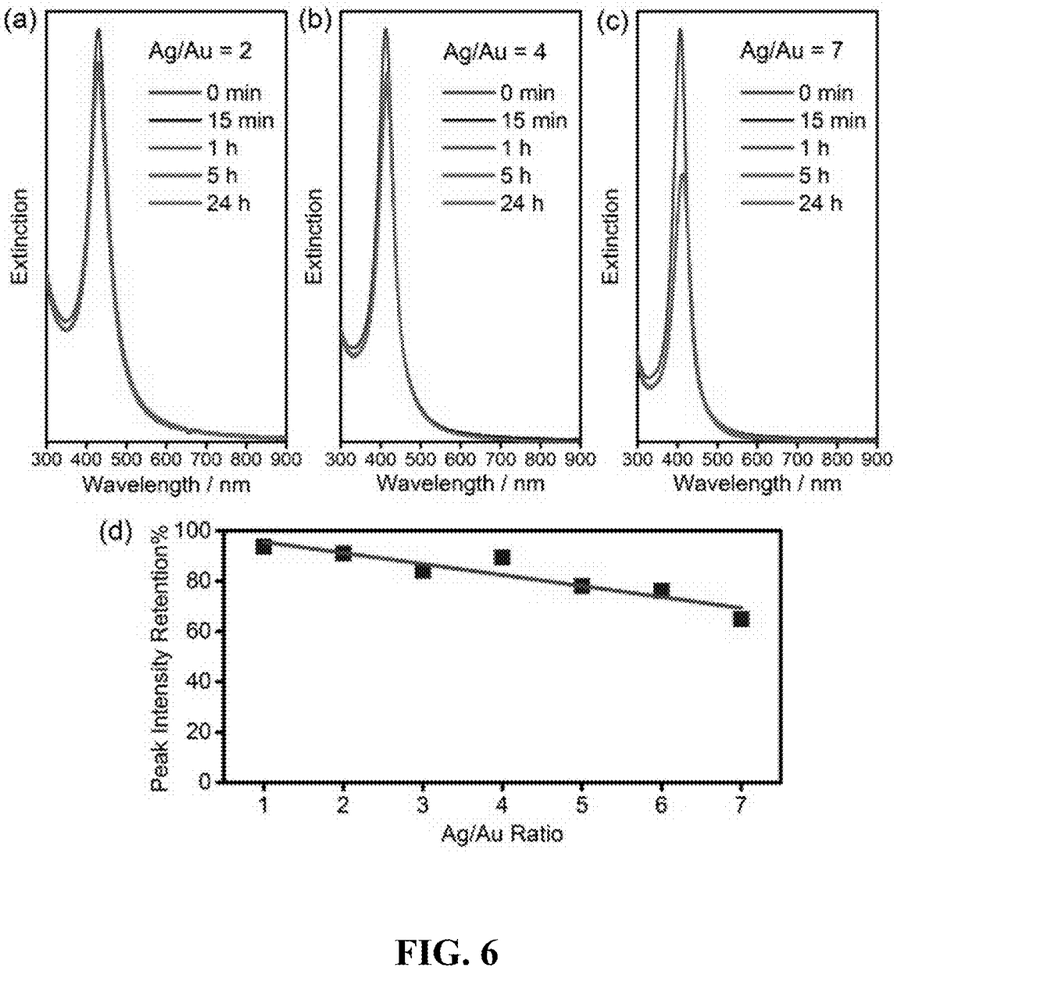
FIG. 6 shows a chemical stability of the Ag/Au alloy nanospheres in an aqueous solution of $H_2O_2$ and $NH_3 \cdot H_2O$, indicated by a UV-Vis spectral change with time, wherein (a-c) Ag/Au=2, 4 and 7, respectively, annealed at 1000° C., and (d) Change of the band intensity after 24 h of etching, relative to their initial intensities.

The stability of the alloy nanospheres also depends on the Ag/Au ratio, and decreases as Ag content increases, as shown in FIG. 6. As an extreme example, UV-vis extinction of Ag/Au alloy nanospheres (Ag/Au=7) retain 65% of their original intensity after 24 hours of etching, although the molar fraction of Au in the nanospheres is only 12.5%. Alloy nanospheres synthesized by the high-temperature annealing method can possess Ag-like plasmonic property and Au-like stability, which may greatly expand their use in many plasmon-based applications especially when corrosive reagents are involved.

Figure 7:
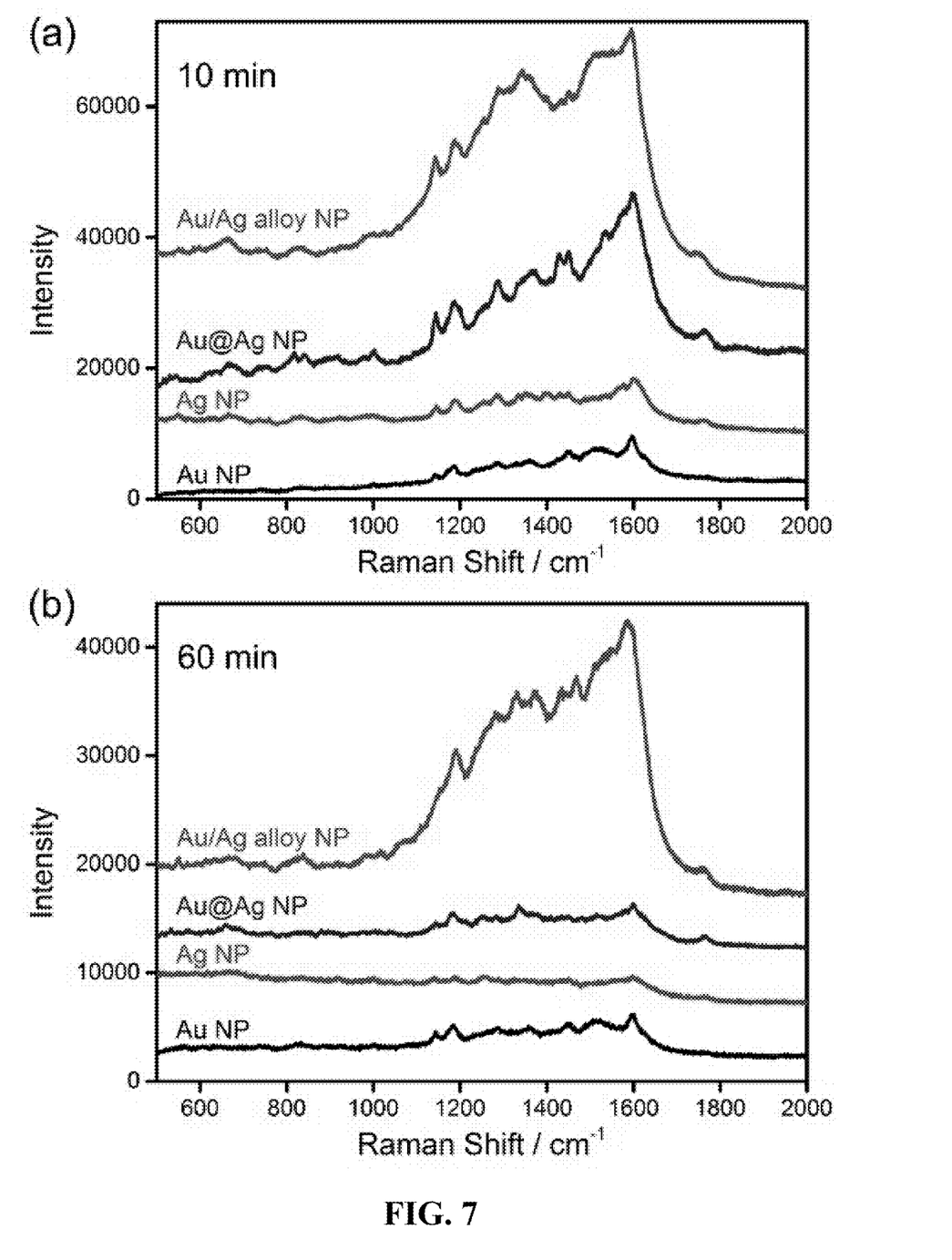
FIG. 7 shows a SERS spectra of benzidine (0.5 μM absorbed from an artificial industrial waste water (NaCl 2 wt %, $H_2O_2$ 1 mM, pH 10) onto a nanoparticle-loaded substrate, showing superior signal enhancement by Ag/Au alloy nanospheres (Ag/Au=5) compared with those by Ag, Au@Ag core/shell or Au nanoparticles, and wherein (a-b), the substrates were soaked in the waste water for 10 min and 60 min, respectively, for loading of benzidine.

In accordance with an exemplary embodiment, to demonstrate the significance of stable alloy nanoparticles in practical applications, a surface-enhanced Raman spectroscopy (SERS) based detection of molecules of interest (benzidine as a model which is a typical dye precursor) from an artificial waste water was devised, as a prototype of pollutant control in dye industry (FIG. 7). These industrial wastes can include salts, oxidants and acids/bases, simulated in our artificial waste water with NaCl (2 wt %), $H_2O_2$ (1 mM) and NaOH (pH 10), respectively, which are often too harsh for Ag-based substrate to survive for a reasonably long soaking time which can be required for molecular loading in SERS analysis. In these circumstances, Ag/Au alloy nanoparticles are advantageous in terms of sensitivity and durability of the detection due to their excellent optical property and stability.

Pure Au, Ag and Au@Ag core/shell nanoparticles of the same size and concentration were used as control for comparison. The Raman signals of benzidine from the Ag or Au@Ag substrates are rapidly damped as the soaking time is prolonged for enhanced molecular loading, which can be attributed to the oxidative etching of Ag in the artificial waste water. Therefore, it is difficult to obtain stable and strong SERS signals from these substrates, which introduces much uncertainty and inaccuracy in molecular detection applications. On the other hand, the Au-substrate gives stable Raman signals, but the signals are relatively weak due to the small extinction cross-sections of the Au nanoparticles. The Raman signals from the substrate of the alloy nanospheres are particularly strong and stable independent of soaking time, which confirms its superior signal enhancement in corrosive media as a result of the large extinction cross-sections (Ag-like) and high stability (Au-like) of the Ag/Au alloy nanospheres.

In accordance with an exemplary embodiment, a high-temperature annealing approach is disclosed, which can produce unprecedentedly fully alloyed Ag/Au nanospheres, which show large cross-sections, narrow bandwidths and high chemical stability. The results indicate that the high mobility of the metal atoms at high temperatures favors homogeneous distribution of the Ag and Au elements over a whole nanosphere and release of crystallographic defects, removing both structural and compositional interfaces, which accounts for the narrow bandwidths of the surface plasmon resonance. The Ag/Au alloy nanospheres are thus concluded to combine the excellent plasmonic property of Ag and the great stability of Au, which may render many plasmonic applications with high performance and long lifetime, especially for those involving corrosive species. A sensitive and etching-resistant SERS detection of molecules from an artificial industrial waste water has been demonstrated in this work, which suggests their promising applications in monitoring pollution in many natural and industrial contexts. It is also expected that the Ag/Au alloy nanospheres may bring benefits to other applications such as solar energy conversion and bio-applications where high plasmonic performance and long chemical stability are critically important. In accordance with an exemplary embodiment, the method disclosed herein can be extended to other metals such as Pt, Pd and Ni for producing high-performance catalysts.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for producing fully alloyed Ag/Au nanospheres, the method comprising:
    forming a stock solution of Au nanoparticles;
    coating the Au nanoparticles with a layer of Ag by mixing the stock solution of Au nanoparticles with solutions comprising a reducing agent and $AgNO_3$, which results in Au@Ag core/shell nanoparticles;
    coating the Au@Ag core/shell nanoparticles with silica to obtain Au@Ag@$SiO_2$ nanoparticles; and
    annealing the Au@Ag@$SiO_2$ nanoparticles at a temperature of at least 930° C.

2. The method of claim 1, wherein the Au nanoparticles are formed by:
    preparing a solution of PVP, ascorbic acid, potassium iodide and $HAuCl_4$ in $H_2O$;
    injecting a seed solution of Au nanoparticles into the solution;
    collecting the Au nanoparticles by centrifugation; and
    redispersing the Au nanoparticles into the stock solution.

3. The method of claim 2, further comprising:
    preparing the seed solution of Au nanoparticles by mixing $HAuCl_4$, $NaBH_4$, and trisodium citrate in $H_2O$.

4. The method of claim 1, wherein the solutions comprising the reducing agent and $AgNO_3$ comprise:
    $H_2O$, PVP, acetonitrile, ascorbic acid, and $AgNO_3$.

5. The method of claim 4, wherein the Au@Ag@SiO$_2$ nanoparticles are formed by:
- adding ethanolic solution to a solution containing the Au@Ag core/shell nanoparticles;
- adding ethanol to a solution containing the ethanolic solution and the Au@Ag core/shell nanoparticles;
- adding TEOS after the adding of the ethanoloic solution and the ethanol under stirring; and
- obtaining the Au@Ag@SiO$_2$ nanoparticles after centrifugation and redispersion.

6. The method of claim 5, wherein the step of annealing comprises:
- drying and annealing the Au@Ag@SiO$_2$ nanoparticles at 1000° C. in a N$_2$ atmosphere to effect alloying of the Ag and Au.

7. The method of claim 6, further comprising:
- redispersing the dried and annealed Au@Ag@SiO$_2$ nanoparticles by sonication of a water solution containing PVP, diethylamine, and NaOH; and
- refluxing the redispersed solution at 100° C. to remove the silica shell.

8. The method of claim 1, wherein the step of coating the Au@Ag core/shell nanoparticles with silica occurs prior to the annealing of the Au@Ag@SiO$_2$ nanoparticles.

9. The method of claim 1, wherein the annealing of the Au@Ag@SiO$_2$ nanoparticles comprises:
- annealing the Au@Ag@SiO$_2$ nanoparticles at about 1000° C.

10. A method for producing fully alloyed Ag/Au nanospheres, the method comprising:
- forming a stock solution of Au nanoparticles;
- coating the Au nanoparticles with a layer of metal by mixing the stock solution of Au nanoparticles with solutions comprising a reducing agent and corresponding salts of the layer of metal, which results in Au@metal core/shell nanoparticles, the metal comprising Pt, Pd, or Ni;
- coating the Au@metal core/shell nanoparticles with silica to obtain Au@metal@SiO$_2$ nanoparticles; and
- annealing the Au@metal@SiO$_2$ nanoparticles at a temperature of at least 930° C.

* * * * *